United States Patent [19]

Silver

[11] 4,430,323

[45] Feb. 7, 1984

[54] METHOD FOR CONTROLLING ORAL MAL ODORS AND DENTAL PLAQUE

[76] Inventor: Jules Silver, 7 Ridgewood Rd., Niantic, Conn. 06357

[21] Appl. No.: 339,381

[22] Filed: Jan. 15, 1982

Related U.S. Application Data

[63] Continuation of Ser. No. 144,929, Apr. 29, 1980, abandoned.

[51] Int. Cl.³ ............................................. A61K 7/18
[52] U.S. Cl. ...................................... 424/52; 424/151
[58] Field of Search ..................................... 424/49–58, 424/151

[56] References Cited

U.S. PATENT DOCUMENTS

| | | | |
|---|---|---|---|
| 2,527,686 | 10/1950 | Sandberg | 424/52 |
| 2,913,373 | 11/1959 | Weisz et al. | 424/52 |
| 3,947,570 | 3/1976 | Pensak et al. | 424/58 |
| 3,975,514 | 8/1976 | Weisz | 424/52 |
| 4,041,149 | 8/1977 | Gaffar et al. | 424/57 |
| 4,097,588 | 6/1978 | Levine | 424/52 |
| 4,150,151 | 4/1979 | Pader et al. | 424/56 |
| 4,183,915 | 1/1980 | Gaffar et al. | 424/52 |

OTHER PUBLICATIONS

Jacobs, "Flavoring Mouthwashes" Amer. Perfumer & Essential Oil Review 61:469,471 Jun. 1953.
JASPD Jan.–Feb. 1975 Everything You Always Wanted to Know About Flouride Therapy (163 Refs.) pp. 17–21, 36–45.
Council on Dental Therapeutics J.A.D.A. 91:1250–1251 Dec. 1975 "Council Classifies Flouride Mouthrinses".

*Primary Examiner*—Shep K. Rose
*Attorney, Agent, or Firm*—Murray & Whisenhunt

[57] ABSTRACT

There is provided a method for the control of oral mal odors by rinsing the oral cavity for a total time period of at least one minute per day and with each rinse time being at least 0.5 minute with an oral rinse consisting essentially of an aqueous solution of 0.01% to 1% of a water-soluble potassium fluoride and/or sodium fluoride. The method also, concurrently, controls calculus formation.

20 Claims, No Drawings

METHOD FOR CONTROLLING ORAL MAL ODORS AND DENTAL PLAQUE

This is a continuation application of Ser. No. 144,929, filed Apr. 29, 1980, now abandoned.

The present invention relates to the method for control of chronic oral mal odors of adults and more particularly to such a method wherein those mal odors are controlled by oral rinsing with a particular aqueous composition, and for minimum oral residence times. Dental calculus is also controlled.

BACKGROUND OF THE INVENTION

Oral mal odors may be broadly separated into two very distinct categories. The first category may be defined as temporary mal odors, which result from a variety of causes. Thus, the ingestion of certain foods, such as highly spiced foods, onion, garlic, excessive alcohol and smoking, and the like, may cause temporary mal odors. In addition, digestive upsets and temporary infections and diseases may cause temporary mal odors.

The second category of mal odors may be defined as chronic mal odors. These mal odors, normally, occur only in the adult population and do not result from transitory causes but result from chronic causes. The exact causes of chronic oral mal odors are not known. They normally occur only in mature adults (25 years of age or older) and are probably a result of specific imbalances in individual oral cavities. Generally speaking, however, chronic mal odors are thought to be caused by the generation of certain odoriferous compounds, among which are sulfides. It is widely believed that the production of these odoriferous compounds results from particular interaction between bacteria normally contained in the mouth and the plaque or calculus on the enamel of the teeth wherein odoriferous compounds, e.g., sulfides are generated. While in most humans, the interaction between the bacteria and the plaque or calculus is not sufficient to generate these odoriferous compounds, in case of chronic oral mal odors, the odoriferous compounds are liberated relatively continuously, presumably by virtue of specific imbalances and bacterial interaction in individual oral cavities. Vigorous brushing and the use of conventional oral rinses are not effective, since the bacterial population is reduced for only a short period of time, and thereafter the odoriferous interaction again commences.

Conventional oral rinses for controlling mal odors may be broadly divided into three categories, i.e., those containing masking agents, such as breath masking flavors, those containing bactericides, and those containing special active ingredients such as enzymes and chlorophyll. These conventional oral rinses, however, are effective for controlling mal odors for only the time period in which the active ingredients are physically in contact with the oral cavity. Unfortunately, that time period is relatively short, since natural salivation quickly washes the active ingredients from the oral cavity. Hence, conventional oral rinses are not effective for controlling chronic mal odors, since the short-lived effectiveness of these rinses requires most frequent treatment of the oral cavity.

A further and relatively new category of oral rinses may be described as fluoride rinses. They are not recognized as oral rinses for controlling mal odors, but, as more fully discussed hereinafter, have been used in dental caries prevention. While these rinses may contain flavors which to a limited degree act as a masking agent, they are not recognized as useful in controlling mal odors, beyond the known effect of the masking agent.

Accordingly, it would be of substantial benefit in the art to provide a method for control of oral mal odors which is suitable for use by those suffering from chronic mal odors and which would provide substantially continuous protection from such oral mal odors without the necessity of frequent treatment of the oral cavity to provide such control.

OBJECTS OF THE INVENTION

It is therefore an object of the invention to provide a method for the control of chronic oral mal odors. More specifically, it is an object of the invention to provide such control of chronic oral mal odors by treating the oral cavity, but without the necessity of frequent treatment of the oral cavity. It is a further object of the invention to provide such method which is convenient to use, may be used during the day in normal privacy periods and is pleasant to administer. It is a further object of the invention to provide such method which concurrently controls dental calculus formation, which in turn serves to reduce chronic mal odors. Other objects will be apparent from the following disclosure and claims.

BRIEF DESCRIPTION OF THE INVENTION

The present invention is based on four primary discoveries. Firstly, it was discovered that certain fluorides are effective in controlling chronic oral mal odors. The mechanism by which the control operates is not fully understood, but it is believed that the control operates by action of the fluorides on the plaque or calculus normally associated with the enamel of the teeth. The fluorides are, apparently, infused into the plaque or calculus and when the infusion is of such concentration, the fluorides so interrupt the interaction between the plaque or calculus and the bacteria that the odoriferous compounds normally associated with the chronic mal odor are not generated, e.g., the sulfides.

Secondly, it was discovered that these fluorides are effective for control of chronic mal odor only when the oral cavity is treated with these fluorides for critical minimum periods of time. If the treatment is for less than these critical minimum periods of time, effective control of the mal odor will not occur.

Thirdly, it was discovered that with these certain fluorides, the level of fluoride, presumably in the plaque, will build with continued use and thereafter mal odor will be controlled even for reasonably longer periods of time without additional use of the fluorides.

Fourthly, it was discovered that with continuous use of the present treatment, the level of the fluorides builds until the fluorides interfere with normal plaque and calculus formation. Thus, the rate of plaque and calculus formation is reduced and the lower level thereof on the teeth results in a decrease of the dental conditions, which, in part, are responsible for chronic oral mal odors.

Thus, briefly stated, the present invention provides a method for control of chronic oral mal odors comprising rinsing the oral cavity for a total time period of at least 1 minute per day and wherein each rinse time is at least 0.5 minute, with an oral rinse consisting essentially of an aqueous solution of 0.01% to 1.0% of a water-soluble fluoride selected from potassium fluoride and sodium fluoride. The rinse may contain optional ingredients which do not affect the basic and novel characteristics of the aqueous solution, e.g., optional flavors, surfactants, preservatives, etc. The method is especially useful for adults suffering from chronic oral mal odors.

DETAILED DESCRIPTION OF THE INVENTION

As is well known in the art, fluoride solutions have been used for caries prevention. For example, U.S. Pat. No. 3,975,514 describes an oral rinse which is said to prevent dental caries of the teeth. The rinse consists of an aqueous solution of water soluble fluorides, sodium chloride and an ionic surface-active wetting agent. A concentration of the fluoride, preferably sodium fluoride, of about 1 grain/ounce (0.2%) is recommended. It is said that the solution retards bacterial growth, exerts a bacterio-static action and inhibits phosphatase. However, fluorides are not generally recognized as effective bactericides. Also, as noted in that patent, prior attempts to use sodium fluoride for preventing dental caries in other compositions, e.g., dentifrices, chewing gum, and the like, have not proved successful. Accordingly, conventional dentifrices which contain fluorides for caries prevention use stannous fluoride, rather than sodium or potassium fluoride, the stannous fluoride being substantially non-water soluble. This anomaly has never been understood in the art.

The Council on Dental Therapeutics reported on tests conducted with fluoride oral rinses for caries prevention, including sodium fluoride, and at varying concentrations, i.e., from as little as 0.01% to as high as 0.225%. Rinsings were conducted as frequently as 2 per day, with the rinse times as great as 2 minutes. However, these tests, run for caries prevention in developing teeth, i.e., subjects between the ages of 5 and 19 years old, did not report any effectiveness of the rinses in the control of chronic mal odors.

The prior art, discussed above, is also silent on the effects on plaque and calculus formation of fluoride containing mouthwashes. Such formations are, especially, problems in mature adults, as opposed to children or young adults.

In spite of all the extensive research concerning fluoride compositions, it has now been surprisingly discovered that certain fluoride oral rinses may be effectively used in a certain method for controlling chronic mal odors, as opposed to temporary mal odors. In this regard, the term "chronic mal odors" is defined to mean those mal odors which are not temporary in nature (induced by temporary diets, smoking, beverages, digestive difficulties, and the like), but are induced by an oral disturbance of a chronic nature wherein the disturbance causes some yet unidentified interaction in the oral cavity, presumably in conjunction with the plaque or calculus, to produce substantially continuous odoriferous compounds, notably among which are sulfides. Chronic oral mal odors are usually occasioned only by mature adults, i.e., adults over the age of approximately 25 years and more often mature adults over the age of 30 years. Accordingly, the term "an adult suffering from chronic oral mal odors" is defined as a human of at least 25 years of age, and more usually at least 30 years of age, who is suffering from chronic oral mal odors as defined above. Thus, the invention is especially useful in the controlling of chronic oral mal odors in adults and this is a preferred form of the invention. The treatment is not necessary for those suffering from temporary oral mal odors, since other treatments are available for those mal odors. As explained hereinafter, the invention also provides the further advantage of controlling plaque and calculus formation, while controlling chronic mal odors.

The oral rinse used in the present method consists essentially of an aqueous solution of 0.01% to 1.0% of a water-soluble fluoride selected from potassium fluoride and sodium fluoride. The solution must be an aqueous solution since it is only the water-soluble fluorides which are effective for present purposes. Non-water-soluble fluorides, e.g., stannous fluoride, calcium fluoride, and the like, are not useful in the present invention. The aqueous solution may contain ingredients other than water, e.g., conventional surfactants, preservatives, colors, bactericides and viscosity control agents, used for their known purposes, but these other ingredients in the present oral rinse will not affect the basic characteristics of the oral rinse. It is in this context that the term "consisting essentially of" is used.

The oral rinse must contain at least 0.01% and up to 1.0% of the water-soluble fluoride. At concentrations less than 0.01%, and therapy is not effective and at concentrations above 1.0%, the danger of unacceptable poisoning (the water-soluble fluorides have some toxicity) is unacceptable. Preferably, for these same reasons, the concentration of fluoride is between 0.05% and 0.5%.

The fluoride, i.e., the potassium or sodium fluoride, may be either the compound per se or the neutralized form thereof, as is known in the art. The fluoride is placed in the aqueous solution simply by mixing and no special process for incorporating the fluoride into the solution is required. This is because the potassium and sodium fluorides are water-soluble and readily go into solution. It is this solubility which also renders the present therapy effective. Less soluble fluorides are not effective for that same reason. The particular mechanism by which these water-soluble fluorides operate is not fully understood, but it is believed that these highly soluble fluorides have the unique ability of entering into the plaque or calculus far more readily than the other fluorides, e.g., stannous fluoride or calcium fluoride, and are therefor effective for controlling chronic oral mal odors.

It has also been discovered that for control of chronic mal odors the time of treatment with the oral rinse is of critical importance. With total time periods of rinsing of less than 1 minute per day, chronic mal odors, particularly chronic mal odors of high levels, can not be controlled. It has also been discovered that within the minimum total time period of rinsing of 1 minute per day, divided rinses must be such that no rinse is less than 0.5 minute. For example, if the 1 minute per day minimum total time period were divided into three rinses, effective control of chronic mal odors would not be achieved. Thus, when the solution is used in rinsing for a minimum of 1 mninute per day total time period of rinsing, two rinses must be used, i.e., to provide at least a 0.5 minute residence with each rinse. It is this critical minimum residence time of the rinse solution that is required for control of chronic mal odors. Rinse times less than these periods may be effective for controlling temporary mal odors, but shorter than 0.5 minute rinse times will not control chronic mal odors. This is a basic discovery of the present invention.

It will also be appreciated that the therapy does require some persistence on the part of the user. Thus, rinsing for at least 1 minute per day and with no individual rinse being less than 0.5 minute is considerably more rinsing than is normally carried out in normal mouthwash rinsing, i.e., normally 15 seconds rinsing time once or twice a day. However, with normal rinsing, the present advantages will not be achieved and the longer total rinse times and critical minimum individual rinse time must be practiced by the recipient in order to achieve the benefits of the present invention.

More preferably, particularly with high levels of chronic mal odors, at least two minutes total rinse time may be necessary, each individual rinse time being at least 1 minute and that rinse is, preferably, performed at least twice a day. While this constitutes a considerable rinse period, for high levels of chronic mal odors, such longer periods are required.

While both the potassium and sodium fluorides are effective in the present method, it is preferred that the fluoride is sodium fluoride. Sodium fluoride is quite soluble in aqueous solutions, produces an acceptable mouth feel of the rinse, and is readily available. Nevertheless, potassium fluoride is quite acceptable in the present method.

Each individual rinse must be sufficient in volume to ensure that essentially the entire surface area of the teeth is thoroughly contacted with the rinse solution. For an adult, for whom the invention is preferred, a minimum volume of three cubic centimeters should be used, although it is preferred that the volume of the rinse is at least five cubic centimeters and more preferably the volume of rinse is from ten cubic centimeters up to as much as thirty cubic centimeters. At volumes above thirty cubic centimeters, the chance of accidental ingestion is increased. It will be appreciated that the rinse is not intended to be ingested.

The frequency in which rinsing must be performed can vary considerably. For lower levels of chronic oral mal odor, rinsing can be as infrequent as every third day. However, normally speaking, for most chronic oral mal odors, the oral cavity is rinsed at least every other day and for more usually encountered cases of chronic oral mal odor, the oral cavity is rinsed daily, all of which rinsing being within the minimum rinse time and total time period explained above.

It should also be appreciated from the foregoing disclosure that the mechanism by which the present method operates depends upon some infusion of the fluoride into the plaque or calculus on the teeth. It has been discovered that this infusion is not immediately displaced, e.g., by salivation and ingestion of food, but residual amounts of fluoride are retained in the plaque or calculus. Thus, over a period of time the level of fluoride in the plaque or calculus will build. After some minimum number of days of rinsing, the level of fluoride in the plaque or calculus will reach that level where the chronic oral mal odors begin to quickly decrease and thereafter the level reaches that point where essentially no mal is present. While at low levels of chronic mal odor the control thereof will be effected after only one day's use, more normally at least 2 days of consecutive use are required before control of the chronic mal odor begins. Thereafter, with treatment the reduction in the chronic mal odor is rapid and will decrease to essentially no mal odor within one to three days. Thus, for the sake of ensuring that no oral mal odor is retained in the oral cavity, rinsing should be continued for at least five consecutive days of rinsing, after which there is no oral mal odor retained in the oral cavity. However, in the more usual cases, there is no oral mal odor retained in the oral cavity after at least three consecutive days of rinsing.

Once the chronic oral mal odor has been reduced to essentially zero by consecutive days of rinsing, that lack of chronic oral mal odor may be maintained with less than daily rinsing, in the manner explained above, i.e., the oral cavity is rinsed at least every third day and more preferably every other day. Nevertheless, as explained above, to ensure that no chronic mal odor reoccurs, daily rinsing is preferred.

As briefly noted above, optional ingredients may be contained in the oral rinse. These ingredients do not affect the basic properties of the rinse used in the present regimen, and the active ingredients of the oral rinse consist essentially of the aqueous solution of fluoride. Nevertheless, if desired, the oral rinse may contain any of the well known wetting agents, such as the non-ionic and anionic surfactants, e.g., esterified and/or ethoxylated alcohols, diamyl or dibutyl sodium sulfosuccinate, isopropylnaphthalene sodium sulfonate and sodium oleiate. Conventional flavors, such as spice and fruit flavors, or other flavors, may be used. Food-grade colors may be used. Conventional preservatives, such as benzalkonium chloride, methyl paraben, and the like may be used. Buffers to provide a pH of between 4 and 7 may also be used, e.g., alkali metal salts, such as phosphates and acetates, and especially $KH_2PO_4$. While explained hereinafter more fully, the inclusion of alkali metal salts, especially phosphates, sulphates and acetates, provide an important advantage beyond the buffering action. Salts of this nature form complex salts with the fluoride salts (presumably in an equilibrium form) which act as an enzyme poison for enzymes in the oral cavity. Additionally, while not desired, viscosity control agents such as glycols, e.g., glycerol, may be used. In addition, while conventional bactericides will not be effective in controlling chronic oral mal odors, they may be used for their conventional bactericidal properties. In this latter regard, a more convenient conventional bactericide is simply ethyl alcohol.

As noted above, continued use of the present fluoride rinse builds the fluoride level in the plaque or calculus to a point where such formation is retarded. The lower rate of such formation correspondingly reduces the amount of plaque or calculus for interaction with oral bacteria. This is a surprising result. Even more surprising is that the accumulated plaque or calculus is easier to remove from the teeth by usual dental procedures. Thus, during normal time periods for calculus removal by usual teeth cleaning procedures, the degree of calculus build-up is substantially decreased and greater control of chronic oral mal odor is achieved. Since substantial calculus formation occurs, normally, only in adults, this effect has not been priorly known, since fluoride rinses have been mainly tested in children and young adults, i.e., under the age of 20, for caries prevention. This unusual result is illustrated in the following example.

The invention will be illustrated by the following examples, which are considered the best modes of the invention, but it is to be understood that the invention is not limited to the specific examples, but extends to the breadth of the foregoing disclosure and the following claims. In the examples, as well as in the specification and claims, all percentages and parts are by weight unless otherwise indicated.

In the examples, it should be noted that Example 1 shows the overall effect of the present method for controlling chronic mal odor in an adult. The Example also uses $KH_2PO_4$. The odor scale used in this example, as well as all of the examples, is the known Odor Intensity Scale, with the usual scale of 0 to 8. The procedure for use of this scale is known and will not be repeated herein for sake of conciseness. Example 1 also compares the ineffectiveness of conventional mouthwashes with the present rinse in that all test subjects were established to have chronic mal odor by first attempting to control the mal odor with conventional mouthwashes. Example 1 also illustrates the presently required rinse times and frequency of rinsing.

Example 2 shows the effectiveness of the present rinse in controlling calculus formation. The test subject was also established to have chronic mal odor. It should be understood that excess calculus formation is commonly encountered in persons suffering with chronic mal odor.

EXAMPLE 1

A solution of sodium fluoride in water was made by dissolving, with stirring, sodium fluoride in water to a concentration of about 0.05%. To this solution was added about 1.4% of $KH_2PO_4$ to buffer the solution to a pH of about 4.5. Methyl paraben was added at about 0.15%, as a preservative, and about 15% sorbitol was added as a sweetener and flavoring agent. The oral rinse was tested for efficacy on the known 0–8 Odor Intensity Scale. On this scale a score of 8 is considered to be an extremely offensive mal odor while 0 is the total absence of mal odor. As is known in the art, obtaining a 0 score is difficult to achieve and most mouthwashes are considered to be satisfactory and effective with a score of about 4.

In the first test, the subject had chronic oral mal odor with an oral factor score of 6. Prior testing showed that the use of conventional mouthwashes in conventional manners were unable to reduce that oral factor score for any significant length of time, e.g., more than ½ hour. The test subject was a mature male who had suffered from chronic mal odor for a considerable length of time.

The test subject was placed on a regimen of rinsing with the rinse solution once per day for 30 seconds. After three consecutive days of rinsing, the test subject still maintained an odor factor score of 4 or above.

The test subject was then placed on a regimen of rinsing with the rinse solution for 30 seconds twice daily. On the first day of rinsing, the oral factor score dropped to 2, and on the second day of rinsing the oral factor score dropped to 0 and thereafter remained at 0 with daily rinsing.

The same oral rinse solution was used on a second adult male test subject with established chronic oral mal odor. The initial odor factor score of the test subject was 6. The subject was placed on the regimen of rinsing for 1 minute once per day. After the first day of rinsing, the odor factor score dropped to 4. After the second day of rinsing, the odor factor score dropped to 1, and after the third day of rinsing, the odor factor score dropped to 0 and remained 0 thereafter.

An adult female test subject was treated with the same oral rinse. This test subject had chronic mal odor for approximately eight consecutive years. Conventional mouthwashes used in conventional manners were ineffective in controlling the oral mal odor for more than about one-half hour to one hour after application. The intensity of the mal odor was so great that the test subject refused to speak to people directly and always turned her head in speaking during conversation, in order to avoid being offensive. The intensity of the mal odor was greater than that normally associated with an oral factor score of 8 and for purposes of this test was ascribed as an oral factor score of 10. In view of the intensity of the chronic oral mal odor, the test subject was placed on a regimen of rinsing with the rinse solution for three minutes three times daily. After rinsing for three consecutive days, the oral factor score dropped to 7; after rinsing for five consecutive days, the oral factor score dropped to 5; after rinsing for seven consecutive days, the oral factor score dropped to 2; and after rinsing for ten (total of ten) consecutive days, the oral factor score dropped to 0 and remained at 0 thereafter with twice daily rinsing.

EXAMPLE 2

An adult male who suffered with chronic oral mal odor also experienced unusually high rates of calculus formation. Although normal calculus removal dental procedures are performed every 9 months to 1 year, in the case of this test subject the calculus removal dental procedure was required every three months and required approximately one hour.

The test subject had not had calculus removed for 3 months. A qualified dentist determined that the calculus build-up was very heavy and one hour was required to remove the calculus. The test subject was placed on regimen of twice daily rinsing for 3 minutes with the solution of Example 1. After 3 months use, the subject was examined by the dentist, who determined that the calculus build-up was quite low and did not require a calculus removal dental procedure. However, to determine the ease of removal of the calculus, the procedure was carried out and the dentist removed the calculus in approximately ten minutes.

Thereafter, the test subject continued the regimen for an additional 6 months. At the end of this period the dentist determined that the calculus build-up was only low to moderate, and again the calculus was removed in approximately 10 minutes. After an additional 12 months of use of the regimen, the dentist again determined that the calculus build-up was moderate and required only 10 minutes to remove.

As can be appreciated from the foregoing, the present invention, i.e., the method, is distinguished from the use of conventional mouthwashes and fluoride mouthwashes in that the invention is directed to those suffering from chronic oral mal odors. The art had not appreciated that the present fluoride mouthwashes are effective in controlling chronic mal odors of all, and especially in intractable, adults. This was a surprising and unexpected discovery, particularly in that this unexpected result is achieved only with the two present water soluble fluorides, as opposed to other possible fluorides known to the art. It will also be appreciated that concurrently with the control of mal odors, control of calculus formation is achieved. This significantly contributes to the long-term control of mal odors and, indeed, has the added and different benefit of improved oral hygiene.

As noted above, while not being bound by theory, it is believed that the present ability to control chronic mal odors with the present method is a result of interaction of the fluoride and the plaque or calculus, the mechanism of which may be the result of enzyme poisoning by the fluoride at the surface of or in the plaque or calculus. Alkali metal salts, e.g., phosphates, sulphates, acetates and the like can form compounds with fluorides. When compounds of this nature are present in the rinse solution, equilibriums between the salts, the re-formed compounds and the fluoride are formed, e.g., ionized or partially ionized sodium mono-fluorophosphate or sodium hexa-fluorophosphate. It is believed that these alkali metal salts and equilibrium compounds play a significant role, in addition to the fluoride salts, in controlling chronic mal odors. Thus, as noted above, it is preferred that the salts be used in the rinse, whether or not they also function as a buffer.

It will also be appreciated from the foregoing examples that for intense mal odors or for severe calculus build-up, the time period of each rinse to provide adequate protection and results is substantially extended, as opposed to the minimum rinse time period of 0.5 minute. Testing has shown that the effectiveness of the method increase with the rinse time period for each rinse and the longer the rinse time period the better. Thus, while for some mild cases of mal odor and calculus built-up, a minimum rinse time period of 0.5 minute is minimally adequate, that minimum rinse time period is not minimally adequate for moderate or severe cases. Thus, in normal practice of the method, a minimum rinse time period of at least 1 minute will be practiced, and most often for adequate results at least 2 minutes will be practiced. However, to insure uniform and predictable benefits for all cases a rinse time period of at least 3 minutes should be practiced. It will be appreciated that in normal use a specific oral factor score for each user will not be established nor will a specific severity of calculus build-up be established, which might show that shorter rinse time periods would be minimally adequate. Thus, in the normal regimen of all un-scored cases, a rinse time period of at least 2 minutes should be used, and optimally at least 3 minutes.

Therefore, the objects of the invention have been met in that there is now provided a method for control of chronic mal odors of persons suffering from chronic mal odor, whereas no such method had previously been described in the art. Having thus accomplished the objects of the invention, the present disclosure provides a substantial advance in the art. However, it will be apparent to those skilled in the art that modifications of the invention may be made without departing from the spirit and scope of the invention as set forth in the foregoing specification and the annexed claims.

What is claimed is:

1. A method for control of chronic oral mal odors of adult persons of at least 25 years of age and suffering from chronic oral mal odors containing oral generated sulfides, comprising rinsing the oral cavity for a total time period of at least 1 minute per day and wherein each rinse time is at least 0.5 minute with an oral rinse where the active ingredient consists essentially of an aqueous solution of 0.01% to 1.0% of a water-soluble fluoride selected from potassium fluoride and sodium fluoride.

2. The method of claim 1 wherein the concentration of the fluoride is between 0.05% and 0.5%.

3. The method of claim 1 wherein the rinse contains one or more of optional flavors, surfactants, preservatives, colors, bactericides and viscosity control agents.

4. The method of claim 1 wherein the fluoride is sodium fluoride.

5. The method of claim 1 wherein the rinse time is at least one minute.

6. The method of claim 5 wherein the rinse is performed at least twice a day.

7. The method of claim 1 wherein the oral cavity is rinsed at least every third day.

8. The method of claim 7 wherein the oral cavity is rinsed at least every other day.

9. The method of claim 8 wherein the oral cavity is rinsed daily.

10. The method of claim 1 wherein the volume of each rinse is at least 3 cc.

11. The method of claim 1 wherein the volume of rinse is at least 5 cc.

12. The method of claim 1 wherein the volume of rinse is from 10 cc to 30 cc.

13. The method of claim 1 wherein no oral mal odor is retained in the oral cavity after at least five consecutive days of rinsing.

14. The method of claim 1 wherein no oral mal odor is retained in the oral cavity after at least three consecutive days of rinsing.

15. The method of claim 1 wherein the oral cavity has a high level of chronic mal odors prior to rinsing.

16. The method of claim 1 wherein the person is an adult.

17. The method of claim 1 wherein the said solution has added thereto a buffer.

18. The method of claim 17 wherein the buffer controls the pH of the solution between a pH of 4 and 7.

19. The method of claim 18 wherein the buffer is an alkali metal salt.

20. The method of claim 19 wherein the said salt is $KH_2PO_4$.

* * * * *